(12) United States Patent
Muppa et al.

(10) Patent No.: US 8,975,423 B2
(45) Date of Patent: Mar. 10, 2015

(54) EPOXIDATION PROCESS

(75) Inventors: Prasad Muppa, Vondelingenplaat (NL); Mark Kapellen, Vondelingenplaat (NL); Caspar Schoolderman, Vondelingenplaat (NL)

(73) Assignee: Hexion Inc., Columbus, OH (US)

( * ) Notice: Subject to any disclaimer, the term of this patent is extended or adjusted under 35 U.S.C. 154(b) by 0 days.

(21) Appl. No.: 13/574,685

(22) PCT Filed: Jan. 26, 2011

(86) PCT No.: PCT/EP2011/000337
§ 371 (c)(1),
(2), (4) Date: Sep. 7, 2012

(87) PCT Pub. No.: WO2011/095296
PCT Pub. Date: Aug. 11, 2011

(65) Prior Publication Data
US 2012/0330042 A1   Dec. 27, 2012

(30) Foreign Application Priority Data
Feb. 2, 2010 (EP) .................................. 100010339

(51) Int. Cl.
*C07D 301/12* (2006.01)

(52) U.S. Cl.
CPC .................................. *C07D 301/12* (2013.01)
USPC ...................................................... 549/531

(58) Field of Classification Search
USPC ...................................................... 549/531
See application file for complete search history.

(56) References Cited

U.S. PATENT DOCUMENTS

| 4,973,718 | A | 11/1990 | Buchler |
| 5,153,161 | A | 10/1992 | Kerschner et al. |
| 5,155,274 | A | 10/1992 | Herrmann et al. |
| 5,274,147 | A | 12/1993 | Kerschner et al. |
| 5,329,024 | A | 7/1994 | Jureller et al. |
| 5,429,769 | A | 7/1995 | Nicholson et al. |
| 5,516,738 | A * | 5/1996 | Jureller et al. ............... 502/155 |
| 5,833,755 | A | 11/1998 | Schlom et al. |
| 6,087,513 | A | 7/2000 | Liao et al. |
| 6,673,950 | B1 | 1/2004 | Teles et al. |
| 2001/0025695 | A1 | 10/2001 | Patt et al. |
| 2002/0010120 | A1 | 1/2002 | Hage et al. |
| 2006/0041150 | A1 | 2/2006 | Catinet et al. |
| 2010/0029848 | A1 | 2/2010 | Forlin et al. |

FOREIGN PATENT DOCUMENTS

| DE | 19923121 | 11/2000 |
| EP | 0458397 | 5/1991 |
| EP | 0458398 | 5/1991 |
| EP | 2149569 | 2/2010 |
| EP | 2149570 | 2/2010 |
| JP | 2002145872 | 5/2002 |

OTHER PUBLICATIONS

J.W. De Boer, University of Groningen, Doctoral disertation (2008).
T.H. Bennur et al., Journal of Molecular Catalysis. A, Chemical, 185 (2002) 71-80.
A. Grenz et al., Chemical Communications (2001) 1726-1727.
Murphy et al., Organic Letters, American Chemical Society, vol. 6, No. 18 (2004) 3119-3122.
Venturello et al., Journal of Organic Chemistry, vol. 48, No. 21 (1983) 3831-3833.
Sibbons et al., Dalton Transactions (2006) 645-661.
Arends et al., Topics in Catalysis, vol. 19, No. 1 (2002) 133-141.
J.W. De Boer at aL, Dalton Transactions (2003) 6283-6295.
Alsters et al., Mechanisms in Homogeneous and Heterogeneous Epoxidation Catalysis, Elsevier Science & Technology (2008) 416-428.
Sherrington et al., Journal of Catalysis, vol. 131, (1991) 115-126.
Mbeleck et al., Reactive & Functional Polymers, 87 (2007) 1448-1457.
A.M. D'A Rocha Gonsalves et al., Journal of Molecular Catalysis A: Chemical, vol. 168 (2001) 25-32.
D.E. De Vos et al., Tetrahedron Letters, vol. 39, No. 20 (1998) 3221-3224.

\* cited by examiner

*Primary Examiner* — T. Victor Oh

(57) ABSTRACT

Processes and compositions are provided for epoxidizing an olefinically unsaturated compound. In one embodiment, a process is provided for reacting an olefinically unsaturated compound with an oxidant in the presence of a catalyst at acidic conditions, wherein the catalyst is activated prior to the reaction at a pH that is higher than the pH during the reaction.

17 Claims, No Drawings

EPOXIDATION PROCESS

RELATED APPLICATION DATA

This application claims the benefit of PCT Application PCT/EP2011/000337 with an International Filing Date of Jan. 26, 2011, published as WO 2011/095296, which PCT Application PCT/EP2011/000337 further claims priority to European Patent Application No. EP10001033.9 filed Feb. 2, 2010, the entire contents of both applications are hereby incorporated by reference.

FIELD OF INVENTION

The current invention relates to a process for oxidation of olefinically unsaturated compounds in the presence of a catalyst.

BACKGROUND OF INVENTION

Epoxidation processes are known. The state of the art comprises for instance Boer de, Johannes W., "cis-Dihydroxylation and Epoxidation of Alkenes by Manganese Catalysts Selectivity, Reactivity and Mechanisms", University of Groningen, 2008. De Boer describes that it is characteristic for the Manganese Catalysts to show a lag period before full reactivity can be observed. The lag period as described above would result in a time of little reaction in a commercial process. Moreover, this lag period can result in unwanted side-reactions and/or will require extra hold up and/or time consuming treatment of the catalyst before it can be (re)used in the reaction process. The provided invention reduces the lag period to a minimum requiring no pre-treatment or hold up time. Moreover, the provided invention results in a better performing catalyst.

DISCLOSURE OF THE INVENTION

Accordingly, the invention provides an epoxidation process comprising a reaction of an olefinically unsaturated compound with an oxidant in the presence of a catalyst at acidic conditions, wherein the catalyst is activated prior to the reaction at a pH that is higher than the pH during the reaction.

In one embodiment, the invention provides a process for forming an epoxide product, comprising reacting a catalyst with an acid or an buffer solution of the acid and a first oxidant comprising a first pH, wherein the catalyst comprises a water-soluble manganese complex having a mononuclear species of the general formula (I): [LMnX$_3$]Y (I), or a binuclear species of the general formula (II): [LMn($\mu$-X)$_3$MnL]Y$_n$(II), wherein Mn is a manganese; L or each L is independently a polydentate ligand, each X is independently a coordinating species and each $\mu$-X is independently a bridging coordinating species, wherein Y comprises a non-coordinating counter ion; and then reacting an olefinically unsaturated compound with a second oxidant in the presence of the catalyst at acidic conditions at a second pH less than the first pH.

MODE(S) FOR CARRYING OUT THE INVENTION

As used in the current specification, the expressions epoxidation and oxidation refer to the same reaction; the conversion of the carbon-carbon double bond of the olefinically unsaturated compound into an oxirane ring. The invention is hereafter discussed in greater detail.

In one embodiment, the invention provides an epoxidation process comprising a reaction of an olefinically unsaturated compound with an oxidant in the presence of a catalyst at acidic conditions. The inventors surprisingly found that a catalyst activated prior to its use in the oxidation reaction is more reactive, such as having a reduced lag time, and is more stable. In particular, the inventors surprisingly found that catalyst activation occurs in a shorter period of time at a higher pH (less acidic pH) than the pH of the epoxidation process, and during the epoxidation process, the catalyst is more stable at a lower pH (more acidic pH) than the pH during the catalytic activation.

The catalyst is activated prior to the epoxidation reaction at a pH that is higher than the pH during the reaction. In one embodiment of the reaction process, the catalyst is activated at a first pH that is at least 0.2 points higher than the second pH during the oxidation reaction. As such, the reaction of the epoxidation process may be carried out at a pH during the oxidation reaction in the range of 1.0 to 6.0 and the catalyst may be activated at a pH that is at least 0.2 points higher than the second pH during the oxidation reaction. In one embodiment, the second pH during the oxidation reaction is in the range of 1.5 to 3.2 and the catalyst is activated at a first pH of 3.3 to 4.5 with the first pH that is at least 0.2 points higher than the second pH.

The catalyst may be activated by contacting the catalyst with an acid or a buffer solution having the acid and an oxidant for at least 5 minutes prior to the reaction. The oxidant may be hydrogen peroxide, such as a dilute hydrogen peroxide, and other suitable oxidants are further described herein with regard to the oxidation of the olefinically unsaturated compound. The same oxidant may be used for activating the catalyst and the oxidation of the olefinically unsaturated compound. After the activation process step, the epoxidation reaction becomes the dominate chemical reaction with continuous dosing of hydrogen peroxide to the reaction mixture. The buffer solution may comprise an organic acid with its corresponding salt, in a ratio corresponding to the desired pH or pH range. Examples of suitable buffer solutions include hydrochloric acid-sodium citrate; oxalic acid-oxalate salt; acetic acid-acetate salt, citric acid-citrate salt, di-sodium phosphate-monosodium phosphate or a mixture thereof.

"Activation," as used herein, is a process in which the metal component of the catalyst is reduced to catalytically active or more catalytically active oxidation states. As the epoxidation reaction is exothermic, the activation time can be defined by tracking the change in exothermic heat formation over time. As a measure for heat formation, the temperature difference between reaction mixture and cooling liquid is used, to be called dT. The definition for activation time can be such as the time from the start of the addition of all raw materials at the reaction temperature, up to the time the maximum dT has been reached, which is an indication that the active catalyst species have been formed.

In one embodiment, the epoxidation catalyst may comprise one or more manganese complexes. The catalyst may be a mononuclear manganese complex or a binuclear manganese complex. Preferred examples thereof include mononuclear species of the general formula (I):

[LMnX$_3$]Y (I), or a binuclear species of the general formula (II):

[LMn($\mu$-X)$_3$MnL]Y$_n$ (II), wherein Mn is a manganese; L or each L is independently a polydentate ligand. Each X is independently a coordinating species and each $\mu$-X is independently a bridging coordinating species, selected from the group consisting of: $RO^-$, $Cl^-$, $Br^-$, $I^-$, $F^-$, $NCS^-$, $N_3^-$, $I_3^-$, $NH_3$, $NR_3$, $RCOO^-$, $RSO_3^-$, $RSO_4^-$, $OH^-$, $O^{2-}$, $O_2^{2-}$, $HOO^-$, $H_2O$, $SH^-$, $CN^-$, $OCN^-$, and $S_4^{2-}$ and combinations thereof, wherein R is a $C_1$-$C_{20}$ radical selected from the group consisting of alkyl, cycloalkyl, aryl, benzyl and combinations thereof. Y is a non-coordinating counter ion. The non-coordinating counter ion Y may provide for the charge neutrality of the complex and the value of n depends upon the charge of the cationic complex and anionic counter ion Y, for example, n may be 1 or 2. Counterion Y may for instance be an anion selected from the group consisting of $RO^{31}$, $Cl^-$, $Br^-$, $I^-$, $F^-$, $SO_4^{2-}$, $RCOO^-$, $PF_6^-$, tosylate, triflate ($CF_3SO_3^-$) and a combination thereof with R once again being a $C_1$ to $C_{20}$ radical selected from the group consisting of alkyl, cycloalkyl, aryl, benzyl and combination thereof. The type of anion is not very critical, although some anions are more preferred than others. In one embodiment, an ion of $CH_3COO^-$ or $PF_6^-$ may be used as the non-coordinating counter ion.

Ligands which are suitable for the present invention are acyclic compounds containing at least 7 atoms in the backbone or cyclic compounds containing at least 9 atoms in the ring, each having the nitrogen atoms separated by at least two carbon atoms. A preferred class of ligands is that based on (substituted) triazacyclononane ("Tacn"). The prefer ligand is TmTacn, which is commercially available from for instance Aldrich. In this respect it is important to note that the water-solubility of the manganese catalyst is a function of all the aforementioned catalyst components.

According to the present invention, the catalyst may be utilized directly or as adsorbed onto a solvent insoluble support surface. Illustrative but non-limiting examples of such substrates are structured aluminosilicates (e.g. Zeolite A, faujasite and sodalite), amorphous aluminosilicates, silica, alumina, charcoal, macroporous polymeric resins (e.g. polystyrene beads formed through high internal phase emulsion technology) and clays (especially layered clays such as hectorite and hydrotalcite). Relative weight ratios of the catalyst to the support may range anywhere from about 10:1 to about 1:10,000.

The catalyst is used in catalytically effective amounts. The catalyst may be used in a molar ratio of catalyst (e.g., Mn) to oxidant (e.g. hydrogen peroxide) of from 1:10 to 1:10,000,000, such as at a molar ratio from 1:100 to 1:1,000,000, for example, at a molar ratio from 1:10,000 to 1:100,000. An advantage of the preferred embodiment of the current invention, using a water soluble manganese complex, is that the catalyst essentially does not migrate to the organic phase.

The epoxidation process may use hydrogen peroxide as the oxidant. Other oxidants may be used, such as a as precursor to the hydrogen peroxide, and given the availability and to reduce environmental impact hydrogen peroxide is the preferred oxidant. Hydrogen peroxide has strong oxidizing properties. The peroxide may be used in an aqueous solution. The concentration of hydrogen peroxide may vary, from 15% to 98% (propellant grade), with a preference for industrial grades varying from 20 to 80%, preferably from 30 to 70%. Other oxidants that may be used include organic peroxides, peracids, and combinations thereof.

The oxidation/epoxidation processes can be carried out in organic solvents as reaction medium, or in an aqueous reaction medium. Indeed, the reaction medium may be a multiphasic reaction medium comprising an aqueous phase and an organic phase. The current epoxidation process may be carried out in an aqueous reaction medium comprising no more than 10 volume percent of co-solvents. The use of organic co-solvents, such as methanol, is believed to improve the solubility of the olefinically unsaturated compound. Suitable co-solvents include, for example, acetone, methanol, and other water-soluble alcohols. The amount of organic co-solvents may be reduced to a minimum and the reaction may be carried out in a reaction medium substantially composed of water. The reaction may be performed in the presence of a phase transfer agent and/or a surfactant.

Insofar as the reaction is carried out in an aqueous reaction medium comprising no more than 10 volume percent of co-solvents, then the manganese complex may be a water-soluble complex. Whilst excluding the presence of the reactants and the epoxidation products, the aqueous reaction medium therefore suitably comprises at least 90% by volume of water (v %), such as at least 95 v %, for example, at least 99 v %, and in some embodiments, at least 99.9 v % of water. Most preferably, however, the aqueous reaction medium (again, excluding any olefins and/or the corresponding oxides dissolved therein) is essentially a 100% water phase.

The aqueous reaction medium may also contain a buffer system, either used to activate the catalyst and retained for the epoxidation reaction, or added at the time of the epoxidation reaction, to stabilize the pH. For instance, it has been found that the aqueous reaction medium is suitably stabilized in a pH range of 1 to 7, whereas the preferred pH range is between 2 and 5. The suitable or preferred range may be achieved by several known organic acid-salt combinations, with the preferred combination being based on oxalic acid-oxalate salt, or acetate acid-acetate salt or oxalic acid-oxalate salt and acetic acid-acetate salt. When oxalic acid and sodium oxalate are used, the pH ratio may be varied from 2.0 to 6.0. The buffer may be used in a molar ratio to the catalyst of about 60:1, but the amounts may be varied broadly, for example, ranging from 1:1 to 300:1.

Various olefinically unsaturated compounds may be epoxidized with an oxidant. In one embodiment, the olefinically unsaturated compound may have at least one unsaturated —C=C— bond, such as at least one unsaturated —C=CH$_2$ group. The olefinically unsaturated compound may comprise more than one unsaturated —C=C— bond. Moreover, the unsaturated —C=C— bond need not be a terminal group. Olefinically unsaturated compounds with at least one terminal —C=CH$_2$ bond are particularly preferred.

Suitable examples of olefinically unsaturated compound therefore include the following compounds:

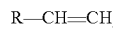

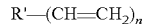

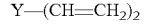

wherein R is a radical of 1 or more carbon atoms optionally comprising 1 or more heteroatoms (such as oxygen, nitrogen or silicon); R' is a multivalent radical of 1 or more carbon atoms optionally comprising 1 or more heteroatoms wherein n corresponds with the valence of the multivalent radical; X is a halogen atom, and Y is an oxygen atom.

Of particular interest are olefinically unsaturated compounds selected from the compounds:
  (a) vinylchloride or allylchloride;
  (b) 1-alkene, preferably propene:
  (c) mono-, di- or polyallyl ethers of mono-, di- or polyols;
  (d) mono-, di- or polyvinyl ethers of mono-, di- or polyols;
  (e) mono-, di- or polyallyl esters of mono-, di- or polyacid;
  (f) mono-, di- or polyvinyl esters of mono-, di- or polyacids;
  (g) divinylether or diallylether.

To achieve the high selectivity and turnover numbers of the current invention, the catalyst and oxidant are preferably combined for reaction with the olefinically unsaturated compound at a molar ratio of catalyst to oxidant from 1:10 to 1:10,000,000, more preferably of from 1:100 to 1:1.000,000, still more preferably of from 1:10,000 to 1:100,000.

The molar ratio of an olefinically unsaturated compound to oxidant affects the reaction and the products of the reaction. For example, if too much oxidant, such as hydrogen peroxide is used, then the selectivity towards the desired epoxide reduces due to the production of undesirable side-products, such as diols, or involves a significant waste of the oxidant. If not enough oxidant is used, then the turnover number is suboptimal. This is therefore significantly different from bleaching conditions described in the prior art, where excessive amounts of an oxidant, such as hydrogen peroxide, are used. The molar ratio of an olefinically unsaturated compound to an oxidant, such as hydrogen peroxide, may be in the range of from greater than 1:2. The molar ratio of an olefinically unsaturated compound to an oxidant, such as hydrogen peroxide, may be in the range of from greater than 1:1.2 to about 12:1, such as from about 1:1 to about 10:1 (or alternatively, from about 1:1.2 to about 2:1, or from 2:1 to 12:1), for example, about 1:1. In one embodiment of the reaction, the olefinically unsaturated compound is preferably used in excess over the oxidant.

The epoxidation process may be carried out in a batch reaction, in a continuous reaction or in a semi-continuous reaction. Depending on the reactants and such, the process may be carried out at a temperature in the range of −40 to 70° C., preferably −5 to 40° C. Moreover, the process may be carried out at reduced pressure or under increased pressure (for instance when propylene is epoxidized).

By way of example, the catalytic epoxidation of allyl chloride is described hereafter.

EXPERIMENTAL

The following examples are illustrative of the invention but not limiting.

The catalytic oxidation was carried out with a binuclear manganese complex $([(TmTacn)_2Mn^{IV}_2(\mu\text{-}O)_3]^{2+}(CH_3COO^-)_2)$ as catalyst of the formula:

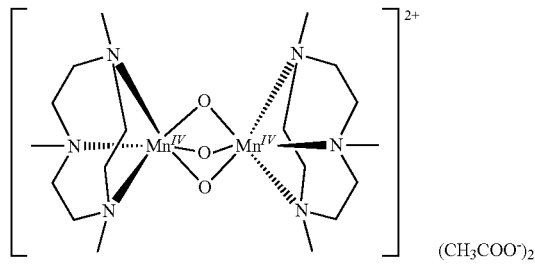

In the examples an oxalate/oxalic acid buffer was used, with 35% aqueous $H_2O_2$ as oxidant, and water (pure) as aqueous reaction medium. The experiments were carried out with allylchloride as starting material. All reactions were performed at 5° C. in a six necked glass reactor facilitated with a mechanical stirrer, cooling jacket and a bottom valve. The molar ratio of catalyst:buffer was 1:180.

All of the experiments were performed with the following processes except when indicated otherwise in the respective example. 100 mL solution of sodium oxalate and oxalic acid were added to the glass reactor, after which about 23 mmol of catalyst was added to the glass reactor under stirring conditions. Then 100 mL allyl chloride was added to the glass reactor and dispersed into the water phase. The reaction was initiated with the addition of dilute $H_2O_2$ as oxidant. Dosing rate is 10 mL/h into the reaction solution. Dosing of oxidant was stopped after 480 min. Because the oxalic buffer is consumed during reaction, a buffer solution at pH=4 was continuously added. The pH was automatically controlled by dosing an oxalic acid solution. After the reaction, the unreacted hydrogen peroxide in the reactor was killed with $Na_2SO_3$. Then, both the water and organic phase were analyzed for Epichlorohydrin.

For evaluating the examples below, the temperature difference (dT) between the reaction mixture and the cooling liquid has been used as a measure for reaction heat, which corresponds to an epoxidation rate. By measuring dT over time, epichlorohydrin formation over time can be determined. Epichlorohydrin formation is then converted to Turn Over Number (TON)=f(t), by dividing epichlorohydrin formed by the amount of catalyst added at t=0. Catalyst activity is defined as dTON/dt. The definition for activation time is the time from the start of the peroxide dosing up to the time the maximum dT has been reached, which is an indication that the active catalyst species have been formed.

Example 1

Comparative

An experiment was performed as described above with the dosing of 10 mL/h of 35 wt % hydrogen peroxide for 480 minutes. At t=0, the starting pH was 3.6 and was maintained at that value for the duration of the reaction. The activation time was observed to be 17 minutes.

Example 2

Comparative

An experiment was performed as described above with the dosing of 10 mL/h of 35 wt % hydrogen peroxide for 480 minutes. At t=0, the starting pH was 3.2 and was maintained at that value for the duration of the reaction. The activation time was observed to be 80 minutes.

Example 3

Illustrative of Invention

An experiment was performed as described above for experiment 1, and with the dosing of 10 mL/h of 35 wt % hydrogen peroxide for 480 minutes. At t=0, the starting pH was 3.6, and at t=15 min, pH was lowered to pH=3.2 and maintained at that value for the duration of the reaction. The activation time was observed to be 17 minutes.

The respective catalytic activities for the three experiments are summarized in Table 1 as follows.

TABLE 1

| Time (min) | Example 1, pH = 3.6 dTON/dT | Example 2, pH = 3.2 dTON/dT | Example 3, pH = 3.6/3.2 dTON/dT |
|---|---|---|---|
| 20 | 78.2 | 5.7 | 76.5 |
| 60 | 58.6 | 25.4 | 57.0 |

TABLE 1-continued

| Time (min) | Example 1, pH = 3.6 dTON/dT | Example 2, pH = 3.2 dTON/dT | Example 3, pH = 3.6/3.2 dTON/dT |
|---|---|---|---|
| 120 | 55.2 | 61.2 | 54.3 |
| 470 | 24.5 | N/A | 30.6 |

When looking at the activation times of examples 1 and 2, the activation time is significantly reduced at a pH of 3.6, with an activation time of 17 minutes, as compared the activation time of a composition having a pH of 3.2, with an activation time of 80 minutes.

While the catalyst activation is faster at pH=3.6 as compared to pH=3.2, it was observed to be beneficial to lower the pH after activation of the catalyst is achieved, as can be seen by comparing example 1 and 3. In both experiments, the catalyst was activated at pH=3.6. However, in example 3, the pH was lowered to 3.2 at t=15 min. Looking at the dTON/dt values for both examples, they are practically identical during the first hours of the reaction. But at the end at t=470 min, dTON/dt for experiment 1 is 25% lower compared to experiment 3. This clearly shows that the catalyst activity has improved reaction stability at a pH of 3.2 as compared to a pH of 3.6.

Additionally, a second set of examples was performed and detailed as follows:

Example 4A

Comparative

Oxalic acid and sodium oxalate were used in a 1:1 molar ratio. The starting pH was 3.0. After 30 minutes of reaction 1857 mol of ECH was produced per mol of catalyst.

Example 4B

Comparative

Oxalic acid and sodium oxalate were used in a 1:1.3 molar ratio. The starting pH was 3.3. After 30 minutes of reaction 2545 mol of ECH was produced per mol of catalyst.

Example 4C

Comparative

Oxalic acid and sodium oxalate were used in a 1:1.8 molar ratio. The starting pH was 3.6. After 30 minutes of reaction 2593 mol of ECH was produced per mol of catalyst.

Comparative examples 4A-4C illustrate that higher rates of reaction can be reached at the same periods of time with an increasing pH of the composition, which is a result on increased activation rates of the catalyst at increasing pH levels.

Example 5

Illustrative of Invention 101.3 mg of oxalic acid and 271.35 mg of sodium oxalate were dissolved in 100 ml water. The oxalic acid and sodium oxalate were in a 1:1.8 molar ratio giving a starting pH of 3.6. After 15 minutes an additional 81 mg of oxalic acid was added to adjust the reaction pH to 3.0. The reaction was observed to have an activation in the first 15 minutes and a continuing high conversion rate after 15 minutes. After 30 minutes of reaction 2882 mol of ECH was produced per mol of catalyst which is significantly higher than the complete reaction at a pH of 3.6.

While the present invention has been described and illustrated by reference to particular embodiments, those of ordinary skill in the art will appreciate that the invention lends itself to variations not necessarily illustrated herein.

What is claimed is:

1. A process for forming an epoxide product, comprising:
    activating a catalyst with an acid or a buffer solution of the acid and a first oxidant at a first pH in the range of 3.3 to 4.5, wherein the catalyst comprises a water-soluble manganese complex having:
    a mononuclear species of the formula (I):

$$[LMnX_3]Y \qquad (I)$$

or a binuclear species of the formula (II):

$$[LMn(\mu\text{-}X)_3MnL]Y_n \qquad (II), \text{ and}$$

wherein Mn is a manganese; each L is independently a polydentate ligand, each X is independently a coordinating species and each μ-X is independently a bridging coordinating species, wherein Y is a non-coordinating counter ion, and n is 1 to 2; and
    reacting an olefinically unsaturated compound with a second oxidant in the presence of the catalyst at acidic conditions at a second pH less than the first pH, wherein first oxidant comprises hydrogen peroxide or dilute hydrogen peroxide and the second oxidant comprises hydrogen peroxide or dilute hydrogen peroxide.

2. The process of claim 1, wherein the second pH is in the range of 1.5 to 3.2 and the catalyst is activated at a first pH that is at least 0.2 higher than the second pH during the reaction.

3. The process of claim 1, wherein the reacting the olefinically unsaturated compound with the second oxidant comprises performing the reaction in an aqueous reaction medium having no more than 10 volume percent of co-solvents.

4. The process of claim 1, wherein the molar ratio of the olefinically unsaturated compound to an oxidant comprising hydrogen peroxide or dilute hydrogen peroxide is from 1:1 to about 12:1.

5. The process of claim 1, wherein the activating the catalyst with the acid or the buffer solution of the acid comprises contacting the catalyst with the acid or the buffer solution of the acid for at least 5 minutes prior to the reacting the olefinically unsaturated compound with the second oxidant in the presence of the catalyst.

6. The process of claim 1, wherein the acid or the buffer solution of the acid comprises a buffer solution of an organic acid with the corresponding organic acid salt.

7. The process of claim 6, wherein the buffer solution comprises a acid-salt buffer selected from the group consisting of hydrochloric acid-sodium citrate; oxalic acid-oxalate salt; acetic acid-acetate salt, citric acid-citrate salt, disodium phosphate-monosodium phosphate, and combinations thereof.

8. The process of claim 1, wherein the first oxidant and the second oxidant comprise hydrogen peroxide.

9. The process of claim 1, wherein the olefinically unsaturated compound has at least one unsaturated —C═C— bond.

10. The process of claim 9, wherein the olefinically unsaturated compound is selected from the compounds:

R—CH=CH$_2$

R'—(CH=CH$_2$)$_n$

X—CH=CH$_2$

Y—(CH=CH$_2$)$_2$ wherein R is a radical of 1 or more carbon atoms optionally having 1 or more heteroatoms; R' is a multivalent radical of 1 or more carbon atoms optionally having 1 or more heteroatoms, wherein n corresponds with the valence of the multivalent radical; X is a halogen atom, and Y is an oxygen atom.

11. The process of claim 10, wherein the olefinically unsaturated compound is selected from the compounds:
(a) vinylchloride or allylchloride;
(b) 1-alkene;
(c) mono-, di- or polyallyl ethers of mono-, di- or polyols;
(d) mono-, di- or polyvinyl ethers of mono-, di- or polyols;
(e) mono-, di- or polyallyl esters of mono-, di- or polyacid;
(f) mono-, di- or polyvinyl esters of mono-, di- or polyacids;
(g) divinylether or diallylether.

12. The process of claim 1, wherein the molar ratio of the olefinically unsaturated compound to the oxidant is from 2:1 to about 10:1.

13. The process of claim 1, wherein each X is independently a coordinating species and each μ-X is independently a bridging coordinating species, selected from the group consisting of: RO$^-$, Cl$^-$, Br$^-$, I$^-$, F, NCS$^-$, N$_3^-$, I$_3^-$, NH$_3$, NR$_3$, RCOO$^-$, RSO$_3^-$, RSO$_4^-$, OH$^-$, O$^{2-}$, O$_2^{2-}$, HOO$^-$, H$_2$O, SH$^-$, CN$^-$, OCN$^-$, and S$_4^{2-}$ and combinations thereof, wherein R is a C$_1$-C$_{20}$ radical selected from the group consisting of alkyl, cycloalkyl, aryl, benzyl and combinations thereof, and Y is a non-coordinating counter ion.

14. The process of claim 13, wherein each polydentate ligand is independently selected from acyclic compounds having at least 7 atoms in the backbone or cyclic compounds having at least 9 atoms in the ring, wherein each polydentate ligand having 3 nitrogen atoms with the nitrogen atoms separated by at least two carbon atoms.

15. The process of claim 1, wherein reacting an olefinically unsaturated compound with a second oxidant comprises performing the reaction in a 100% water phase excluding the presence of the reactants and the epoxidation products.

16. The process of claim 1, where the buffer to catalyst molar ratio ranges from 1:1 to 300:1.

17. The process of claim 1, wherein the non-coordinating counter ion is an anion selected from the group consisting of RO$^-$, Cl$^-$, Br$^-$, I$^-$, F, SO$_4^{2-}$, RCOO$^-$, PF$_6^-$, tosylate, triflate (CF$_3$SO$_3^-$) and a combination thereof with R once again being a C$_1$ to C$_{20}$ radical selected from the group consisting of alkyl, cycloalkyl, aryl, benzyl and combination thereof.

* * * * *